United States Patent
Otiaba

(10) Patent No.: US 12,213,532 B2
(45) Date of Patent: Feb. 4, 2025

(54) ELECTRONIC VAPOR PROVISION SYSTEM

(71) Applicant: Nicoventures Trading Limited, London (GB)

(72) Inventor: Kenny Otiaba, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 18/329,693

(22) Filed: Jun. 6, 2023

(65) Prior Publication Data

US 2023/0318024 A1    Oct. 5, 2023

Related U.S. Application Data

(63) Continuation of application No. 16/949,216, filed on Oct. 20, 2020, now Pat. No. 11,710,848, which is a
(Continued)

(30) Foreign Application Priority Data

Aug. 25, 2015 (GB) ................................ 1515087

(51) Int. Cl.
| | |
|---|---|
| *A24F 40/50* | (2020.01) |
| *A24F 40/90* | (2020.01) |
| *H01M 4/58* | (2010.01) |
| *H01M 10/0525* | (2010.01) |
| *H01M 10/42* | (2006.01) |
| *H01M 10/44* | (2006.01) |

(Continued)

(52) U.S. Cl.
CPC .............. *A24F 40/50* (2020.01); *A24F 40/90* (2020.01); *H01M 4/5825* (2013.01); *H01M 10/0525* (2013.01); *H01M 10/42* (2013.01); *H01M 10/44* (2013.01); *H02J 7/345* (2013.01); *A24F 40/10* (2020.01); *A61M 11/042* (2014.02); *A61M 15/06* (2013.01); *H01M 2004/028* (2013.01); *H01M 2220/30* (2013.01)

(58) Field of Classification Search
None
See application file for complete search history.

(56) References Cited

U.S. PATENT DOCUMENTS

| | | |
|---|---|---|
| 9,402,422 B2 | 8/2016 | Shenkal |
| 9,775,380 B2 | 10/2017 | Fernando et al. |

(Continued)

FOREIGN PATENT DOCUMENTS

| | | |
|---|---|---|
| AU | 2013314436 A1 | 4/2015 |
| AU | 2016313251 B2 | 12/2019 |

(Continued)

OTHER PUBLICATIONS

Chilean Office Action, Application No. 201800498, dated Aug. 7, 2019, 7 pages.

(Continued)

*Primary Examiner* — James Harvey
(74) *Attorney, Agent, or Firm* — Husch Blackwell

(57) ABSTRACT

A control unit for an electronic vapor provision system includes a battery for providing electrical power to a heater which is used to produce vapor. The battery is a lithium iron phosphate battery. The battery provides an output voltage which remains at an approximately constant voltage level as the battery is discharged.

22 Claims, 7 Drawing Sheets

Related U.S. Application Data continuation of application No. 15/754,349, filed as application No. PCT/GB2016/052624 on Aug. 24, 2016, now Pat. No. 10,806,180.

(51) Int. Cl.
*H02J 7/34* (2006.01)
*A24F 40/10* (2020.01)
*A61M 11/04* (2006.01)
*A61M 15/06* (2006.01)
*H01M 4/02* (2006.01)

(56) References Cited

U.S. PATENT DOCUMENTS

| | | | |
|---|---|---|---|
| 10,181,621 B2 | 1/2019 | Paolella et al. | |
| 10,326,117 B1 | 6/2019 | Lennox et al. | |
| 11,503,672 B2 | 11/2022 | Chen et al. | |
| 2013/0255702 A1* | 10/2013 | Griffith, Jr. | A24F 15/01 |
| | | | 131/328 |
| 2013/0319440 A1 | 12/2013 | Capuano | |
| 2014/0147718 A1 | 5/2014 | Furui et al. | |
| 2015/0230521 A1 | 8/2015 | Talon | |
| 2016/0345628 A1* | 12/2016 | Sabet | H04M 1/21 |
| 2017/0110767 A1 | 4/2017 | Paolella et al. | |
| 2017/0367410 A1 | 12/2017 | Hon | |
| 2018/0242635 A1 | 8/2018 | Otiaba | |
| 2020/0014011 A1 | 1/2020 | Wollfarth et al. | |
| 2020/0028171 A1 | 1/2020 | Huang et al. | |
| 2021/0137172 A1 | 5/2021 | Otiaba | |
| 2023/0318024 A1* | 10/2023 | Otiaba | H01M 10/44 |
| | | | 131/329 |

FOREIGN PATENT DOCUMENTS

| | | |
|---|---|---|
| CN | 103415222 A | 11/2013 |
| CN | 203789154 U | 8/2014 |
| CN | 104055224 A | 9/2014 |
| CN | 104066345 A | 9/2014 |
| CN | 204116873 U | 1/2015 |
| CN | 104486956 A | 4/2015 |
| CN | 104584366 A | 4/2015 |
| EP | 2454956 A1 | 5/2012 |
| EP | 2701268 A1 | 2/2014 |
| JP | 2013127897 A | 6/2013 |
| JP | 2014504886 A | 2/2014 |
| JP | 2015503916 A | 2/2015 |
| WO | 2012109371 A2 | 8/2012 |
| WO | 2013040275 A1 | 3/2013 |
| WO | 2013076098 A2 | 5/2013 |
| WO | 2014040988 A2 | 3/2014 |
| WO | 2015101479 A1 | 7/2015 |
| WO | 2015107551 A2 | 7/2015 |
| WO | 2015117702 A1 | 8/2015 |
| WO | 2015165812 A1 | 11/2015 |
| WO | 2015177045 A1 | 11/2015 |

OTHER PUBLICATIONS

First Office Action for Chinese Application No. 201680048889.8 dated Oct. 30, 2019, 13 pages.
Great Britain Search Report, Application No. GB1515087.3, dated Jan. 28, 2016, 5 pages.
International Preliminary Report on Patentability, Application No. PCT/GB2016/052624, mailed Nov. 21, 2017, 9 pages.
International Search Report and Written Opinion, International Application No. PCT/GB2016/052624, mailed Nov. 22, 2016, 11 pages.
Japanese Office Action, Application No. 2018-510072, dated Jan. 15, 2019, 7 pages.
Japanese Office Action, Application No. 2018-510072, dated Sep. 1, 2020, 10 pages.
Korean Office Action, Application No. 10-2018-7005486, dated Jan. 31, 2019, 12 pages.
Notification to Grant Patent Right for Invention for Chinese Application No. 201680048889.8 dated Apr. 29, 2020, 7 pages.
Westcott R, "Batteries on planes pose 'increased fire risk'", BBC Transport Correspondent News article dated Feb. 4, 2014 entitled (http://www.bbc.co.uk/news/business-25733346), 3 pages.
Albright, Greg, Jake Edie, and S, "A comparison of lead acid to lithium-ion in stationary storage applications", All Cell Technologies LLC, Mar. 2012.
Safari, et al., "Modeling of a Commercial Graphite/LiFePO4 Cell", Journal of Electrochemical Society, vol. 158, No. 5, 2011, pp. A562-A571.
Summons to Attend Oral Proceedings received for European Patent Application No. 16758243.6, mailed on Feb. 4, 2021, 7 pages.

* cited by examiner

| | | | | | | | | | | | |
|---|---|---|---|---|---|---|---|---|---|---|---|
| 2.90 | 2.88 | 2.87 | 2.87 | 2.87 | 2.87 | 2.87 | 2.87 | 2.87 | 2.88 | *2.88* | *0.03* |
| 2.89 | 2.87 | 2.89 | 2.89 | 2.89 | 2.89 | - | 2.89 | 2.89 | 2.89 | *2.89* | *0.05* |
| 2.89 | 2.89 | 2.89 | 2.89 | 2.89 | 2.89 | 2.88 | 2.89 | 2.89 | 2.89 | *2.89* | *0.04* |
| 2.88 | 2.88 | 2.88 | 2.88 | 2.88 | 2.88 | 2.88 | 2.88 | 2.88 | 2.87 | *2.88* | *0.02* |
| 2.87 | 2.89 | 2.89 | 2.89 | 2.89 | 2.88 | 2.88 | 2.88 | 2.88 | 2.87 | *2.88* | *0.05* |
| 2.89 | 2.90 | 2.89 | 2.89 | 2.89 | 2.89 | 2.88 | 2.88 | 2.88 | 2.88 | *2.89* | *0.04* |
| 2.88 | 2.87 | 2.87 | 2.86 | 2.86 | 2.86 | 2.85 | 2.85 | 2.85 | 2.87 | *2.86* | *0.04* |
| 2.86 | 2.87 | 2.86 | 2.86 | 2.85 | 2.85 | 2.85 | 2.84 | - | 2.82 | *2.85* | *0.08* |
| 2.82 | 2.82 | 2.81 | 2.80 | 2.79 | 2.78 | 2.77 | 2.77 | 2.76 | 2.75 | *2.79* | *0.09* |
| 2.74 | 2.74 | 2.73 | 2.72 | 2.71 | 2.70 | 2.68 | 2.67 | 2.73 | 2.73 | *2.72* | *0.12* |
| 2.71 | 2.70 | 2.69 | 2.68 | 2.66 | 2.62 | | | | | *2.68* | *0.24* |

Table 1

FIG. 10

ELECTRONIC VAPOR PROVISION SYSTEM

PRIORITY CLAIM

The present application is a continuation application of U.S. patent application Ser. No. 16/949,216, filed Oct. 20, 2020, which is a continuation application of U.S. patent application Ser. No. 15/754,349, filed Feb. 22, 2018, which is a National Phase entry of PCT Application No. PCT/GB2016/052624, filed Aug. 24, 2016, which claims priority from GB Patent Application No. 1515087.3, filed Aug. 25, 2015, each of which is hereby fully incorporated herein by reference.

FIELD

The present disclosure relates to an electronic vapor provision system, e.g. an e-cigarette, and to a control unit for such a system.

BACKGROUND

Electronic vapor provision systems such as e-cigarettes and other electronic nicotine delivery systems generally contain a cartridge to provide a reservoir of liquid which is to be vaporized, typically nicotine. When a user inhales on the device, a control unit operates a battery to provide power to a heater. This activates the heater to vaporize a small amount of liquid, which is then inhaled by the user.

This type of e-cigarette therefore generally incorporates two consumables, firstly the liquid to be vaporized, and secondly power in the battery. Regarding the former, once the reservoir of liquid has been exhausted, at least a portion of the device containing the cartridge may be discarded to allow replacement with a new cartridge. Regarding the latter, an e-cigarette usually provides some form of electrical connector to receive power from an external charging device, thereby allowing the battery with the e-cigarette to be re-charged.

Most e-cigarettes are powered by re-chargeable lithium ion batteries (or cells), which are to be found in a very widespread range of devices, not just e-cigarettes. (N.B. the terms "battery" and "cell" will be used inter-changeably herein, since due to the limited space within an e-cigarette, the battery in such an e-cigarette usually comprises just a single cell.) Conventional (commonly-used) lithium ion batteries are based on a cathode made from lithium cobalt oxide ($LiCoO_2$), and produce a voltage output that tends to decline as they discharge, for example, from about 4.2V when fully charged, down to about 3.0V before being fully depleted, i.e. a decline of about 28%. Furthermore, since the power output across a given heating resistor R goes with $V^2/R$, this implies that there would generally be a corresponding drop in power output such that the final operational power output (at a voltage of 3.0V) is only 52% of the initial power output (at a voltage of 4.2V). This change in power supplied by the battery to the heater, from being fully charged to being nearly discharged, can therefore significantly impact the amount of liquid vaporized, and hence inhaled by a user.

Existing e-cigarettes have adopted a number of techniques for coping with this variation in power supplied by a battery over the discharge cycle. For example, some devices may shut themselves down before the battery falls to 3.0V—e.g. at a battery output voltage of 3.6V. This reduces the variation in power output (the final operational power output is now at about 73% of the maximum value for a 3.6V cut-off). On the other hand, part of the energy stored within the battery is no longer available for use, which reduces the time that the device can be operated without having to then re-charge.

Other devices employ a capacitor to store additional charge from the battery. By suitable switching the capacitor can then be used as an additional (temporary) power source to supplement the voltage available from the battery. This supplementary power (voltage) from the capacitor can thereby help to compensate for the reduced voltage available from the battery in the latter stages of the discharge cycle.

Another approach is to use a pulse width modulation (PWM) scheme, in which the power is supplied from the battery as a succession of rectangular pulses. If the duration (width) of each pulse is P, and the pulse interval from the end of one pulse to the start of the next pulse is I, then we can define the PWM duty cycle (D) as $D=P/(P+I)$. The duty cycle goes to zero as the pulse width P goes to zero, i.e. in this case the battery is effectively not supplying power. Conversely, the duty cycle goes to unity as the pulse interval I goes to zero, i.e. in this case the battery is effectively supplying continuous (unmodulated) power. If the voltage output from the battery is V, where $3.6<V<4.2$, then we can set the duty cycle D such that the effective voltage output, DV, has a constant value, for example, 3.6V. In particular, if the current voltage output from the battery is V=3.6, i.e. the battery is nearly depleted, the PWM is set such that D=1, while if the current voltage output from the battery is V=4.2, i.e. the battery is fully charged, the PWM is set such that D=0.857 (with intermediate values of D as appropriate for intermediate values of the battery output voltage).

Note that a PWM scheme to control the output of voltage from the battery may be used for more general control purposes (rather than specifically to compensate for variation in battery voltage output). For example, the heater power output may be measured, such as by using some form of thermometer, or by electrically monitoring the current and/or voltage supplied to the heater. The PWM duty cycle may then be controlled to obtain a desired output temperature from the heater. It will be appreciated that such a control system may accommodate variations in battery voltage output along with other potential variations (such as external temperature, type of liquid to be vaporized, etc.). Furthermore, such a control system may use some other mechanism (not PWM) to regulate the effective output voltage and power from the battery.

Existing schemes to accommodate variations in battery output voltage have certain drawbacks. For example, they usually require additional components in the e-cigarette, which adds to complexity and cost. Moreover, a PWM system (or similar) may constrain power based on the lowest battery output voltage (v=3.6). In other words, at higher levels of available battery output voltage (such as V=4.2), the available output voltage is reduced (by PWM or any other suitable mechanism), which effectively chokes back the performance. Such an approach therefore prevents a user from experiencing the operation of the device at full battery voltage.

SUMMARY

The disclosure is defined in the appended claims.

A control unit for an electronic vapor provision system includes a battery for providing electrical power to a heater which is used to produce vapor. The battery is a lithium iron phosphate battery. The battery provides an output voltage which remains at an approximately constant voltage level as the battery is discharged.

An electronic vapor provision system is also provided which includes such a control unit.

BRIEF DESCRIPTION OF THE DRAWINGS

Various embodiments of the disclosure will now be described in detail by way of example only with reference to the following drawings:

FIG. 10 is a tabular representation of the experimental data shown in FIG. 7.

DETAILED DESCRIPTION

As described above, the present disclosure relates to a battery-powered electronic vapor provision system, such as an e-cigarette. Throughout the following description the term "e-cigarette" is used; however, this term may be used interchangeably with electronic vapor provision system. Such an electronic vapor provision system may be based, for example, on the vaporization (by heating) of a liquid, where the liquid includes nicotine, and a user then inhales the resulting vapor containing nicotine. Another possibility is that the electronic vapor provision system includes material derived from tobacco plants. This tobacco material may be provided in any suitable form (powder, paste, shredded leaf material, etc.). The tobacco material may be heated to produce volatiles for inhalation by a user. The skilled person will be aware of various other forms of electronic vapor provision system which can utilize battery power as described herein for heating a substance to produce vapor.

Figure 1:
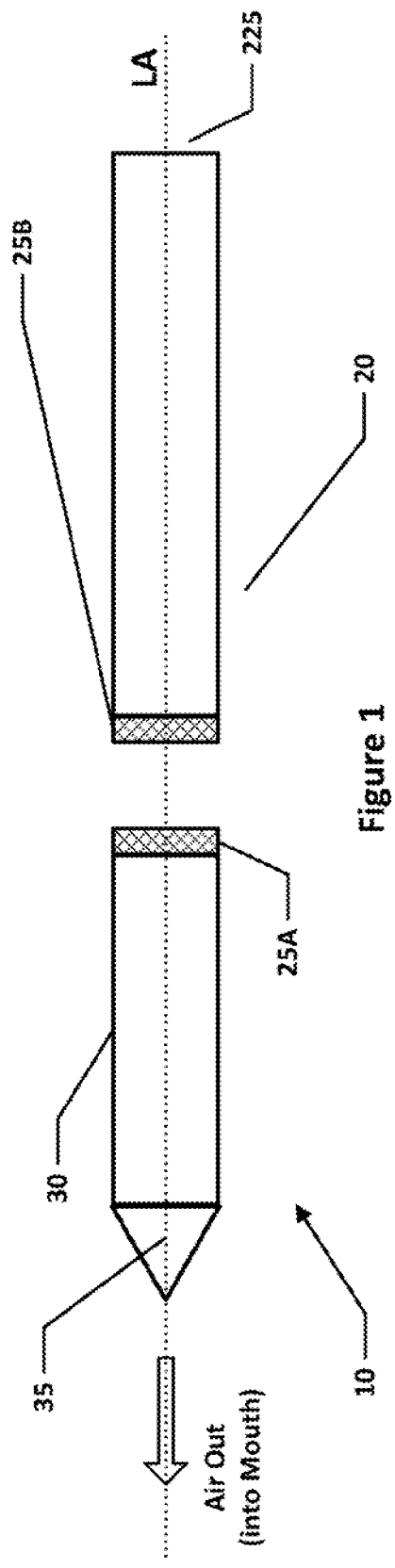
FIG. 1 is a schematic (exploded) diagram of an e-cigarette in accordance with some embodiments of the disclosure.

FIG. 1 is a schematic (exploded) diagram of an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer 30 includes an internal chamber containing a reservoir of liquid, a vaporizer (such as a heater), and a mouthpiece 35. The liquid in the reservoir typically includes nicotine in an appropriate solvent, and may include further constituents, for example, to aid aerosol formation, and/or for additional flavoring. The reservoir may include a foam matrix or any other structure for retaining the liquid until such time that it is required to be delivered to the vaporizer. The cartomizer 30 may further include a wick or similar facility to transport a small amount of liquid from the reservoir to a heating location on or adjacent the heater. The control unit 20 includes a re-chargeable cell or battery to provide power to the e-cigarette 10 and a circuit board for generally controlling the e-cigarette 10. When the heater receives power from the battery, as controlled by the circuit board, the heater vaporizes the liquid from the wick and this vapor is then inhaled by a user through the mouthpiece 35.

The control unit 20 and cartomizer 30 are detachable from one another by separating in a direction parallel to the longitudinal axis (LA) of the e-cigarette 10, as shown in FIG. 1, but are joined together when the device 10 is in use by a connection, indicated schematically in FIG. 1 as 25A and 25B, such as a bayonet or screw fitting. This connection provides mechanical and electrical connectivity between the body 20 and the cartomizer 30. The electrical connector on the body 20 that is used to connect to the cartomizer may also serve as a socket for connecting a charging device (not shown) when the body 20 is detached from the cartomizer 30. The other end of the charging device can be plugged into a USB socket to re-charge the battery in the control unit 20 of the e-cigarette 10. In other implementations, a cable may be provided for direct connection between the electrical connector on the body 20 and a USB socket. In other implementations, the re-charging of the battery in the control unit 20 may be performed via the tip end 225 of the e-cigarette 10, i.e. the end opposite to the mouthpiece 35.

The control unit 20 is provided with one or more holes (not shown in FIG. 1) for air inlet. These holes connect to an air passage through the control unit 20 to an air passage provided through the connector 25. This then links to an air path through the cartomizer 30 to the mouthpiece 35. When a user inhales through the mouthpiece 35, air is drawn into the control unit 20 through the one or more air inlet holes, which are suitably located on the outside of the e-cigarette 10. This airflow (or the resulting change in pressure) is detected by a pressure sensor that in turn activates the heater to vaporize the liquid from the reservoir (via the wick). The airflow passes from the control unit, through the vaporizer, where it combines with the vapor, and this combination of airflow and (nicotine) vapor then passes through the cartomizer 30 and out of the mouthpiece 35 to be inhaled by a user. The cartomizer 30 may be detached from the body 20 and disposed of when the supply of liquid is exhausted and replaced with another cartomizer 30, if so desired. (The cartomizer 30 may therefore sometimes be referred to as a disposable component, and the control unit 20 as a re-usable component.)

It will be appreciated that the e-cigarette 10 shown in FIG. 1 is presented by way of example, and various other implementations can be adopted. For example, in some embodiments, the cartomizer 30 is provided as two separable components, namely a cartridge comprising the nicotine reservoir and mouthpiece (which can be replaced when the liquid from the reservoir is exhausted), and a vaporizer comprising a heater (which is generally retained). As another example, the charging facility may connect to an additional or alternative power source, such as a car cigarette lighter.

Figure 2:
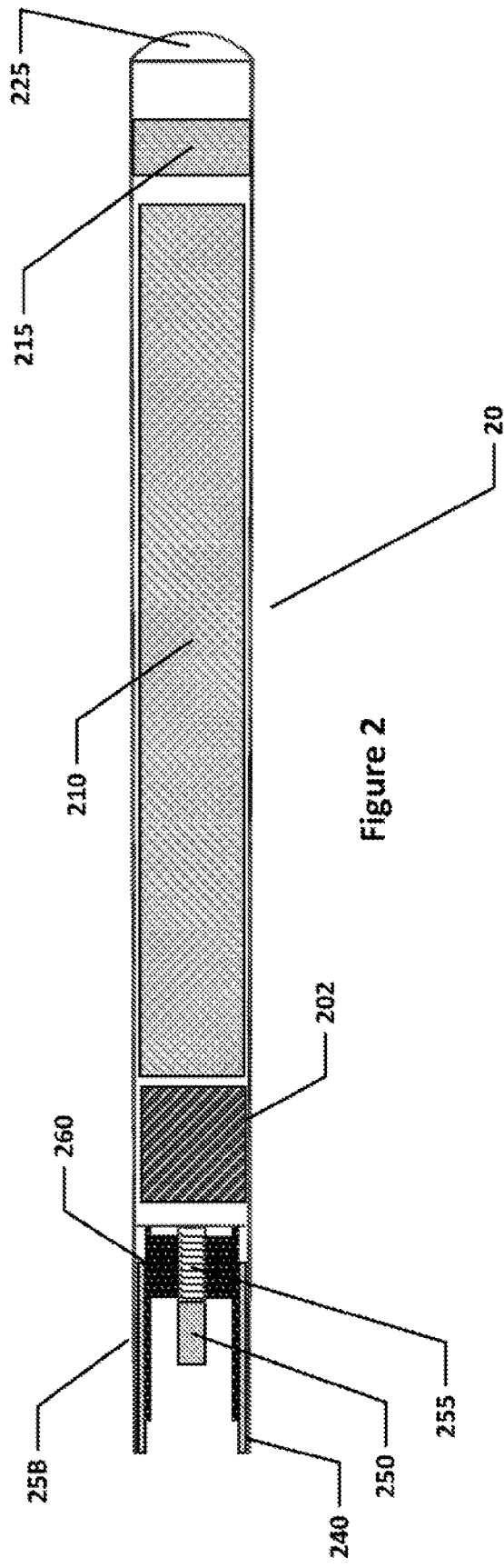
FIG. 2 is a schematic diagram of the body of the e-cigarette of FIG. 1 in accordance with some embodiments of the disclosure.

FIG. 2 is a schematic (simplified) diagram of the control unit 20 of the e-cigarette 10 of FIG. 1 in accordance with some embodiments. FIG. 2 can generally be regarded as a cross-section in a plane through the longitudinal axis LA of the e-cigarette 10. Note that certain components and details of the body 20, e.g. wiring and more complex shaping, have been omitted from FIG. 2 for reasons of clarity.

As shown in FIG. 2, the control unit 20 includes a battery 210 for powering the e-cigarette 10, as well as a printed circuit board (PCB) 202 on which is mounted a chip, such as an application specific integrated circuit (ASIC) or microcontroller, for controlling the e-cigarette 10. The PCB 202 may be positioned alongside or at one end of the battery 210. In the configuration shown in FIG. 2, the PCB 202 is located between the battery 210 and the connector 25B. The control unit also includes a sensor unit 215 to detect an inhalation on mouthpiece 35. In the configuration shown in FIG. 2, the sensor unit 215 is located between the battery 210 and the tip end 225, but in other implementations, it may be located on or adjacent to PCB 202 (which may be positioned as shown in FIG. 2, or in some other location). In response to such a detection of inhalation, the sensor unit 215 notifies the chip on the PCB 202, which in turn initiates the flow of power from the battery 210 to a heater in the cartomizer 30.

The tip end 225 of the control unit 20 includes a cap to seal and protect the far (distal) end of the e-cigarette 10. There is an air inlet hole provided in or adjacent to the cap to allow air to enter the body 20 and flow past the sensor unit 215 when a user inhales on the mouthpiece 35. This airflow therefore allows the sensor unit 215 to detect the user inhalation. In some implementations, the tip end 225 may be provided with a light, such as a light emitting diode (LED) that is illuminated by the chip in response to the detection of inhalation by the sensor unit 225. The tip end 225 may also (or alternatively) be provided with an electrical contact (not shown in FIG. 2) to provide an additional connection for re-charging battery 210.

At the opposite end of the body 20 from the tip end 225 is the connector 25B for joining the control unit 20 to the cartomizer 30. As noted above, the connector 25B provides mechanical and electrical connectivity between the control unit 20 and the cartomizer 30. As shown in FIG. 2, the connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The connector 240 generally has an annular ring shape, while contact 250 is located in the center of this ring (when seen in a plane which is perpendicular to the longitudinal axis, LA, of the e-cigarette 10).

The electrical contact 250 is mounted on a coil spring 255. When the control unit 20 is attached to the cartomizer 30, the connector 25A on the cartomizer pushes against the electrical contact 250 in such a manner as to compress the coil spring 255 in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the control unit 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

Figure 3:
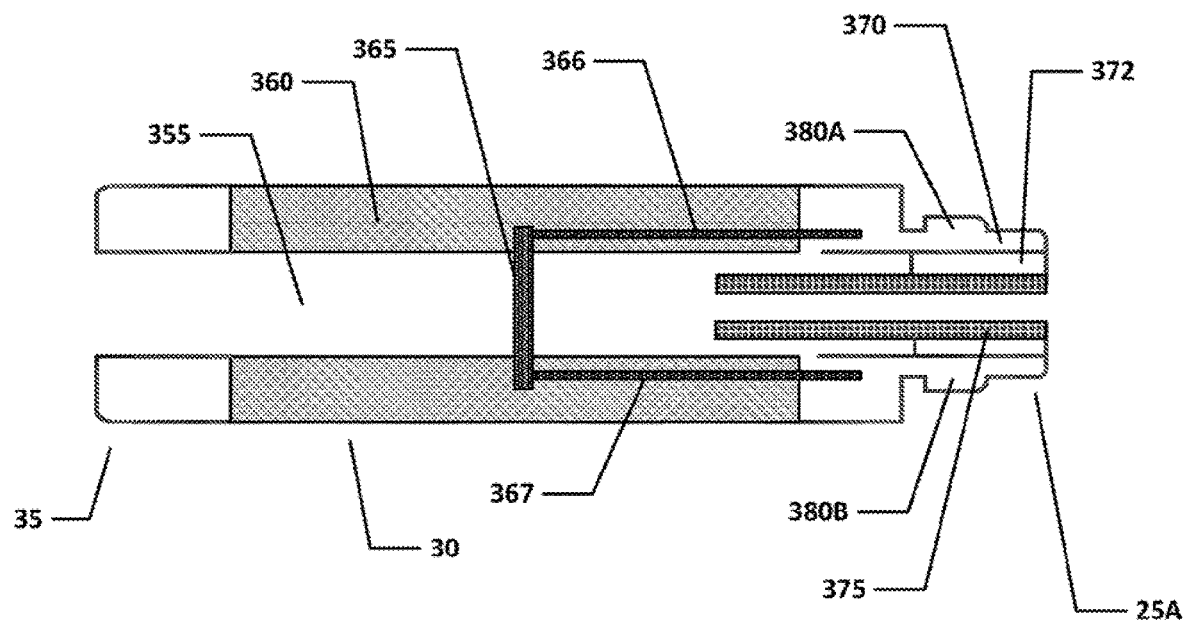
FIG. 3 is a schematic diagram of the cartomizer of the e-cigarette of FIG. 1 in accordance with some embodiments of the disclosure.

FIG. 3 is a schematic diagram of the cartomizer 30 of the e-cigarette 10 of FIG. 1 in accordance with some embodiments of the disclosure. FIG. 3 can generally be regarded as a cross-section in a plane which includes the longitudinal axis LA of the e-cigarette 10. Note that various components and details of the control unit 20, e.g. wiring and more complex shaping, have again been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer to the control unit 20. A reservoir of liquid 360 (typically including nicotine in a solvent) is provided around the air passage 335. This reservoir 360 may be implemented, for example, by providing cotton or foam soaked in the liquid. The cartomizer 30 also includes a heater 365 for heating the liquid from reservoir 360 to generate (nicotine-containing) vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 via connector 25A. (As noted above, the details of the wiring between the power lines 366 and 367 and connector 25A are omitted from FIG. 3.)

The connector 25A includes an inner electrode 375, which may be silver-plated or made of some other suitable metal. When the cartomizer 30 is connected to the control unit 20, the inner electrode 375 contacts the electrical contact 250 of the control unit 20 to provide a first electrical path between the cartomizer 30 and the control unit 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring 372 is surrounded by the cartomizer connector 370, which may be silver-plated or made of some other suitable metal or conducting material. When the cartomizer 30 is connected to the control unit 20, the cartomizer connector 370 contacts the body connector 240 of the control unit 20 to provide a second electrical path between the cartomizer 30 and the control unit 20. In other words, the inner electrode 375 and the cartomizer connector 370 serve as positive and negative terminals (or vice versa) for supplying power from the battery 210 in the control unit 20 to the heater 365 in the cartomizer 30 via supply lines 366 and 367 as appropriate.

The cartomizer connector 370 is provided with two lugs or tabs 380A, 380B, which extend in opposite directions away from the longitudinal axis LA of the e-cigarette 10. These tabs 380A, 380B are used to provide a bayonet fitting in conjunction with the body connector 240 for connecting the cartomizer 30 to the control unit 20. This bayonet fitting provides a secure and robust connection between the cartomizer 30 and the control unit 20, so that the cartomizer 30 and control unit 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the control unit 20 and the cartomizer 30, such as a snap fit or a screw connection.

Figure 4:
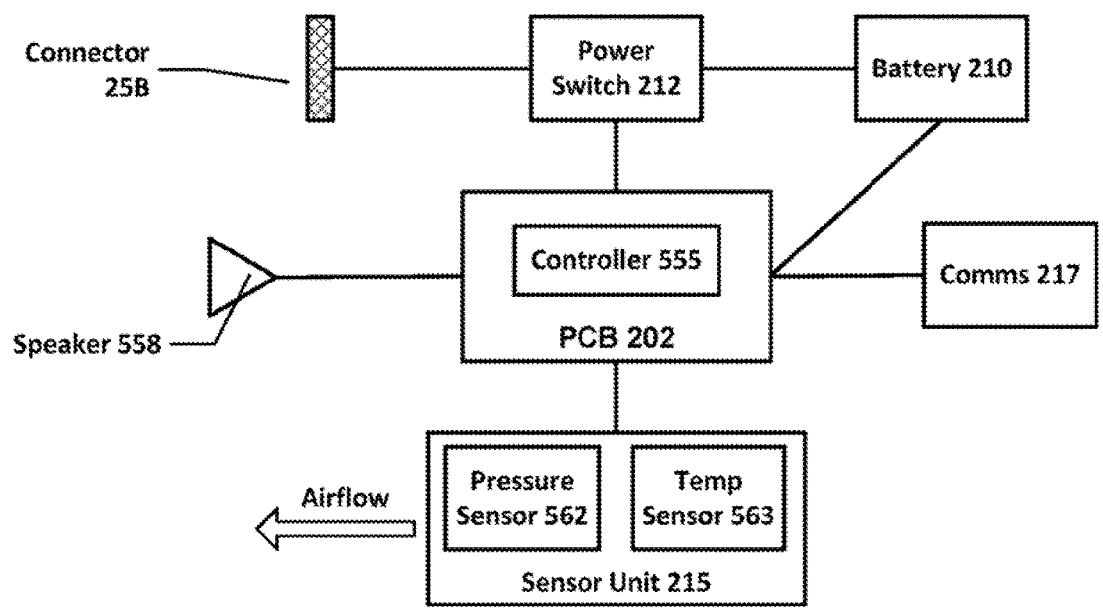
FIG. 4 is a schematic diagram of certain electrical components of the e-cigarette of FIG. 1 in accordance with some embodiments of the disclosure.

FIG. 4 is a schematic diagram of certain electrical (including electronic) components of the e-cigarette 10 of FIG. 1 in accordance with some embodiments of the disclosure. These components are generally located in the control unit 20, since this is a re-usable (rather than disposable) portion. However, in some embodiments at least, some of the electrical components may be located in the cartomizer 30.

As shown in FIG. 4, the control unit 20 includes an electrical (and mechanical) connector 25B (as discussed above), a power switch 212, a battery 210, a processor or (micro)controller 555, a communications interface 217, a speaker 558, and a sensor unit 215. The controller 555 is located on PCB 202, which may also be used for mounting other components as appropriate, e.g. sensor unit 215, power switch 212, and/or communications interface 217, depending upon the particular internal configuration of the control unit 202. Alternatively, these components may be located on one or more other PCBs (or other forms of mounting).

FIG. 4 illustrates some, but not necessarily all, of the electrical connections between the different components. For example, the sensor unit 215 may receive power from the battery 210 via its connection to the controller 555, or alternatively there may be a separate power connection from the battery 210 direct to the sensor unit 215 (not shown).

The sensor unit 215 is located in or adjacent to the air path through the control unit 20 from the air inlet to the air outlet (to the vaporizer). The sensor unit 215 includes a pressure sensor 562 and a temperature sensor 563 (also in or adjacent to this air path). Note that in some embodiments, there may be additional sensors (not shown in FIG. 4); also, the pressure sensor 562 and temperature sensor 563 may be provided as different devices (rather than being combined into a single sensor unit). The pressure sensor 562 may detect airflow by looking for a pressure drop caused by inhalation on the mouthpiece 35 (or alternatively the pressure sensor 562 may detect an inhalation by directly measuring airflow, analogous to an anemometer measuring wind).

The controller 555 includes a processor such as a CPU and memory (ROM and RAM). The operations of the controller 555 and other electronic components, such as the pressure sensor 562, are generally controlled at least in part by software programs running on the processor (or on the other electronic components as appropriate). Such software programs may be stored in a non-volatile memory, such as ROM, which can be integrated into the controller 555 itself, or provided as a separate component (e.g. on PCB 202). The processor may access the ROM to load and execute individual software programs as and when required. The controller 555 also contains suitable interfaces (and control software) for interacting with the other devices, such as with the sensor unit 215.

The controller 555 utilizes the speaker 58 as an output device for producing audio signals to indicate conditions or states within the e-cigarette 10, such as a low battery warning. Different signals for signaling different states or conditions may be provided by utilizing tones or beeps of different pitch and/or duration, and/or by providing multiple such beeps or tones. Other forms of output device may be provided as well as or instead of the speaker 58. For example, as mentioned above the tip end 225 may be provided with a light emitting diode (LED) which may be used for signaling and/or ornamentation. There may also (or alternatively) be a light output at one or more other locations on the e-cigarette 10.

The communications interface 217 may be a wired or wireless connection to allow the e-cigarette 10 to communicate with an external device. For example, the communications interface 217 may support one or more of Bluetooth, Wi-Fi (the IEEE 802.11 family), and/or near field communications (NFC) for establishing wireless communications. Alternatively, or additionally, the communications link may support wired communications, potentially via connector 25B and/or some other communications facility. The communications interface 217 may be used, inter alia, to allow an external device to provide and update control settings on the e-cigarette 10, and/or to retrieve status and usage information from the e-cigarette 10.

As noted above, the e-cigarette 10 provides an air path from the air inlet through the e-cigarette 10, past the pressure sensor 562 and the heater 365 (in the vaporizer), to the mouthpiece 35. Thus when a user inhales on the mouthpiece 35 of the e-cigarette 10, the controller 555 detects such inhalation based on information from the pressure sensor 562. In response to such a detection, the CPU supplies power from the battery or cell 210 to the heater 365, which thereby heats and vaporizes the liquid from the wick for inhalation by the user.

The battery 210 is linked to the heater 365 via a power switch 212 and connector 25B (plus connector 25A on the cartomizer 30). The power switch 212 supports the flow (and switching on/off) of the relatively large current supplied from the battery 210 in order to power the heater 365—this is typically of the order of 1 amp or more. The power switch 212 is controlled by the controller 555. For example, the controller 555 may close the power switch 212 in response to the pressure sensor 562 sensing an airflow through the e-cigarette 10, thereby allowing power to flow from the battery 210 to the heater 365. Conversely, the controller 555 may open the power switch 212 in response to the pressure sensor 562 sensing that the airflow through the e-cigarette 10 has now ended, thereby terminating the power flow from the battery 210 to the heater 365. In addition, the controller 555 may use switch 212 to implement a PWM scheme, as described above, to regulate the amount of power supplied from the battery 210 to the heater 365 during an inhalation.

It will be appreciated that the electrical configuration shown in FIG. 4 is provided by way of example only, and the skilled person will be aware of many potential variations. For example, some e-cigarettes 10 may not have a communications interface 217, while in other embodiments, the communications interface 217 may be combined, at least in part, with the controller 555. Similarly, some of the functionality of the controller 555 may be distributed across one or more other devices. For example, there may be a PCB provided in combination with battery 210 to control re-charging of the battery 210, such as to detect and thereby prevent voltage or current overload and/or overly long charging, and likewise to control discharging of the battery 210, e.g. so that the battery does not get excessively discharged to the point of damage. Such battery control functions may also be integrated into the processor or controller 555 (or into some other device).

The battery 210 is a lithium iron phosphate (LFP) battery which uses lithium ferrophosphate, $LiFePO_4$, for the cathode. LFP batteries have certain advantages and disadvantages compared with other available batteries, such as other types of lithium ion batteries, including the commonly used cobalt cathode battery, or variants thereof (e.g. having a solid rather than liquid electrolyte, or using a silicon anode rather than a graphite anode). However, it has been found that the properties of LFP batteries are particularly well-suited for use in an e-cigarette, based (primarily) on the following factors:

non-toxicity. This is important for a product which is used (albeit not consumed) orally, for example, if the product has been inadvertently damaged. The lack of toxicity also gives improved environment properties (compared to cobalt as used in most common lithium ion batteries), especially since e-cigarettes are a relatively high-volume, low cost product, and may not always be disposed of in an approved manner—e.g. if the product is accidentally dropped or otherwise lost while outside.

thermal, electro-chemical, and structural stability. The thermal stability is important for a product which is used in (and hence exposed to) a wide range of weathers and temperature conditions. Also the good electrochemical and mechanical stability reduces the risk of fire, etc., which has been a problem for most common lithium ion batteries, as reported, for example, on 4 Feb. 2014 in "Batteries on planes pose 'increased fire risk'" (http://www.bbc.co.uk/news/business-25733346).

constant discharge voltage. As noted above, most common lithium ion batteries tend to have an output voltage that decreases steadily over the discharge cycle from about 4.2V down to about 3.6V. This can lead to an inconsistent user experience in terms of supplied vapor (dependent on the current voltage level), or else require an e-cigarette to incorporate appropriate electronics to compensate for this decrease in output voltage, which leads to additional expense and complexity (in what is a relatively high-volume, low cost product).

high peak current/power. LFP batteries can support a higher peak current (and hence higher peak power) than most common lithium ion batteries. This is attractive for e-cigarettes, because it allows the heater to power up more quickly to the correct operating temperature for vaporization in response to the detection of a user inhalation, and hence makes the e-cigarette more user-responsive.

a slower rate of capacity loss (self-discharge) when the battery is not in use. This gives improved shelf (calendar) life if a product is to be supplied ready-charged (which is the case for many e-cigarettes in order to allow for rapid use after purchase by a consumer).

a large number of re-charge cycles are possible—e.g. up to or over 2000. This gives several years of use even if re-charging occurs on a daily basis (see below).

LFP batteries do have a lower energy density than most common lithium ion batteries. However, whereas most common lithium ion batteries are utilized in electronic devices that may be subject to continuous and intensive use (such as smartphones), so that battery lifetime is especially significant in such devices, e-cigarettes tend to have a different usage profile. In particular, there is an interval between successive activations (puffs) of an e-cigarette, and indeed some e-cigarettes may provide protection against over-use, e.g. by monitoring and regulating for a maximum number of puffs in a given time period (after which the processor may prevent further activation until the time period has expired). Accordingly, the lower energy density of LFP batteries (compared with most common lithium ion batteries) is more acceptable for e-cigarettes than for most other electronic devices.

Nevertheless, LFP batteries do have sufficient energy density to support reasonable use of an e-cigarette. For example, an AA-sized LFP battery may have a rated capacity of 250-600 mA hours, whereas a corresponding commonly-used lithium ion battery may have a rated capacity of 600-750 mA hours or more (and operate at a higher voltage), depending on factors such as discharge current. Of course, some e-cigarettes may be too small for an AA-sized battery, and accordingly their battery capacity would have to be reduced accordingly. Nevertheless, given that a typical puff of a regular e-cigarette uses of the order of 1-4 mA hours (depending on the particular nature of the device and the amount of liquid to be vaporized), a reasonably-sized LFP battery is capable of providing at least 100 puffs (and potentially many more) before discharging. Therefore, if we assume that the e-cigarette is re-charged on a daily basis, this number of puffs per battery charge cycle is sufficient for most consumers.

Figure 5:
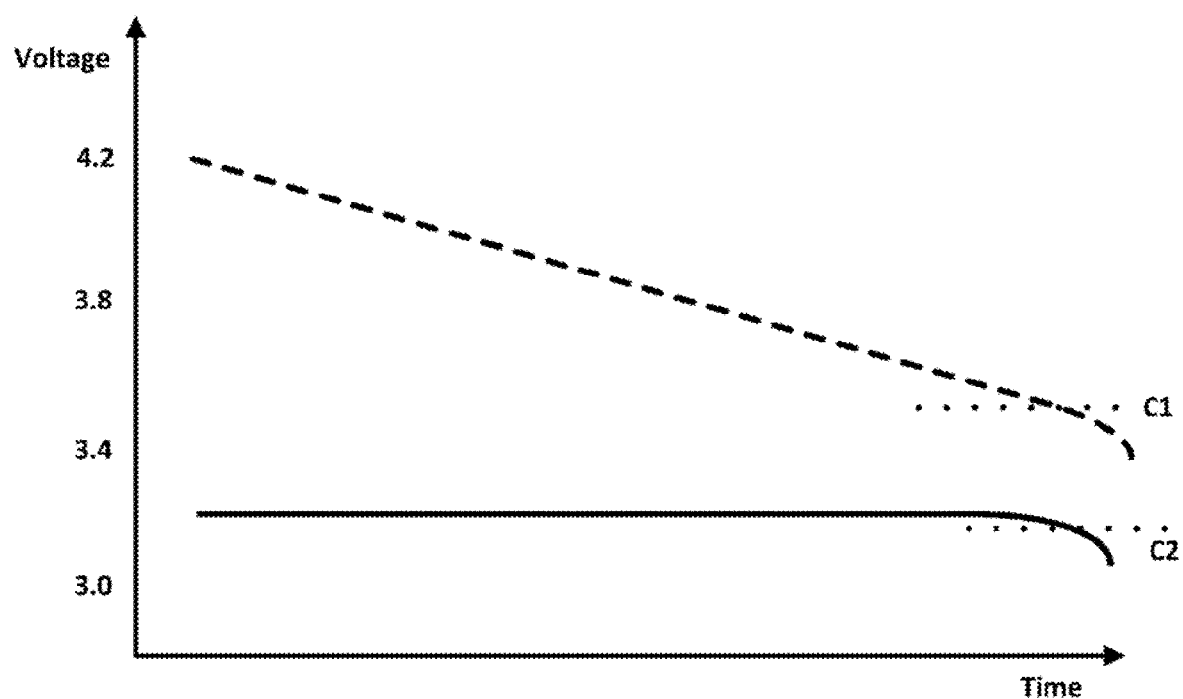
FIGS. 5 and 6 are schematic graphs that compare certain operational properties of an LFP battery (solid line) with those of a commonly used lithium ion battery (dashed line) in the context of e-cigarettes.
Figure 6:
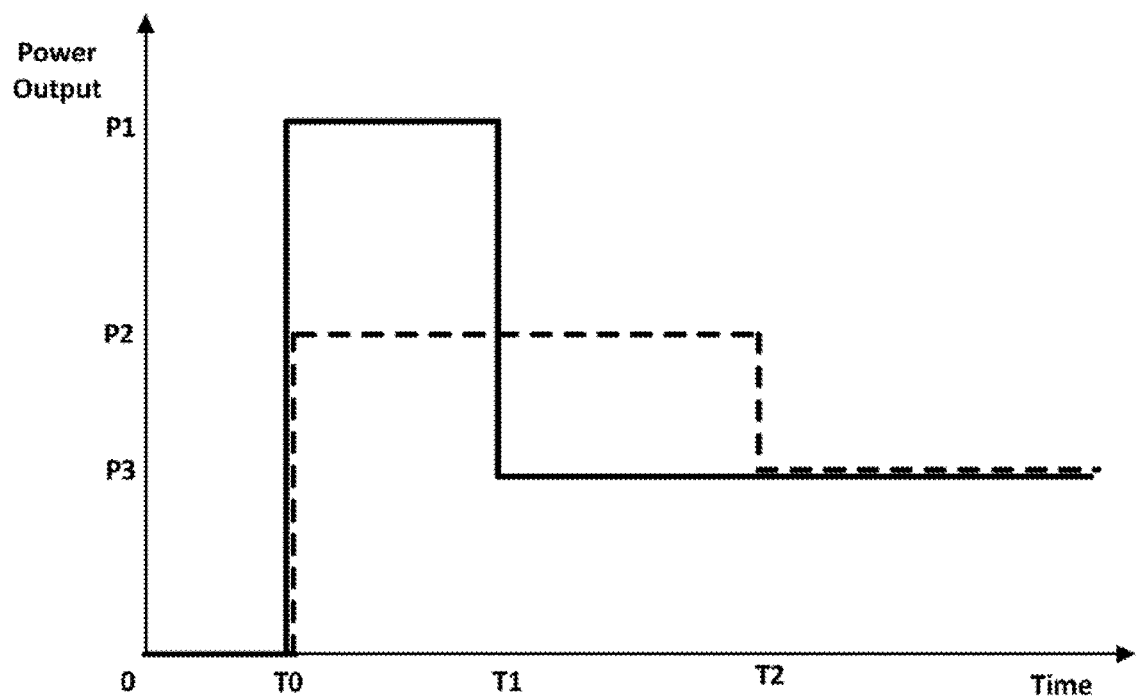

FIGS. 5 and 6 are graphs that compare certain operational properties of an LFP battery (solid line) with those of a commonly-used lithium ion battery (dashed line) in the context of e-cigarettes. (Please note that these graphs are highly schematic and simplified for ease of understanding; some more accurate graphs are presented below.) FIG. 5 illustrates in schematic form how the voltage output of the battery 210 varies with time, typically over a timescale of many hours or days during the discharge cycle (from fully charged to discharged). As discussed above, as a commonly-used lithium ion battery discharges, the output voltage steadily declines from about 4.2V down to about 3.6V (or below). This decline in output voltage may result in a noticeable change (drop) in performance, such as the amount of nicotine vapor produced per puff, over the discharge cycle of the battery (unless some additional compensatory methods are employed to counter this decline). In contrast, the output voltage of an LFP battery is much more constant at around 3.2V, thereby providing a user with a more consistent and reliable experience, while avoiding the need for any additional compensation of the declining voltage. (Note that the voltage levels shown in FIGS. 5 and 6 are for an open circuit condition; the voltage under load will be somewhat lower—e.g. approximately by about 0.5V, so 2.7V for the LFP battery compared with 3.2V for an open circuit.)

FIG. 5 also shows two cut-off lines, marked as C1 and C2. The processor 555 (or some other facility within the control unit 20), monitors the voltage output from the battery 210. When the voltage output falls below the specified cut-off level, C1 or C2 (for a commonly-used lithium ion battery or an LFP battery respectively), the processor 555 prevents further operation of the e-cigarette 10, and more specifically of heater 365. This cut-off, which can be regarded as the end of the discharge cycle, therefore protects the battery 210 from excessive discharge (which may cause damage to a re-chargeable battery), as well as ensuring that the user does not receive a compromised experience from the e-cigarette 10 due to the device operating at an unsuitably low voltage. Note that as discussed above, the controller 555 may provide some user indication of the battery status (exhausted, or near exhausted) via speaker 558 (and/or via any other available indicator).

FIG. 6 illustrates in schematic form how the power output of the battery 210 may vary over a timescale of a single puff, i.e. just a few seconds (this can be regarded as a form of puff profile). The graph compares the operation (in terms of current output) of a commonly-used lithium ion battery (dashed line) against the corresponding performance of an LFP battery (solid line) for an e-cigarette 10.

We assume in FIG. 6 that an inhalation is initiated and detected by a suitable sensor at time=T0. At this point, the controller 555 enables the maximum available power from the battery 210 to be supplied to the heater 365. The maximum available power from an LFP battery is shown as P1 in FIG. 6, while the maximum available power from a commonly-used lithium ion battery is lower, shown as P2 (where P1>P2). For example, the maximum power output P1 for the LFP battery may reflect a current of at least 2.5 A, or at least 5 A, potentially up to a maximum of several amps (e.g. 6, 8 or 10 amps).

At time T1 the heater reaches its preferred operating temperature (for the e-cigarette having an LFP battery), and the power now falls to a lower level P3, which is set so as to maintain the heater at the preferred operating temperature. Similarly, for an e-cigarette having a commonly-used lithium ion battery, the heater reaches its preferred operating temperature at time T2, and the power again falls to level P3 so as to maintain the heater at the preferred operating temperature.

Since the maximum power output P1 of the LFP battery is greater than the maximum power output P2 of a commonly-used lithium ion battery, the time T1 taken for an e-cigarette using the former to reach the preferred operating temperature is less than the time T2 taken for an e-cigarette using the latter to reach the preferred operating temperature. Accordingly, an e-cigarette having an LFP battery can provide better responsiveness to a user inhalation than an e-cigarette having a commonly-used lithium ion battery.

Note that different types of electrical product present different types of load to a battery regarding timing and amount of current draw. For example, a bicycle lamp will tend to have a prolonged draw (many minutes) at low to moderate current, whereas an e-cigarette generally utilizes short pulses of high current for inhalation, with a low level of current draw between the pulses. These differing load characteristics may have an effect on overall battery behavior.

Figure 7:
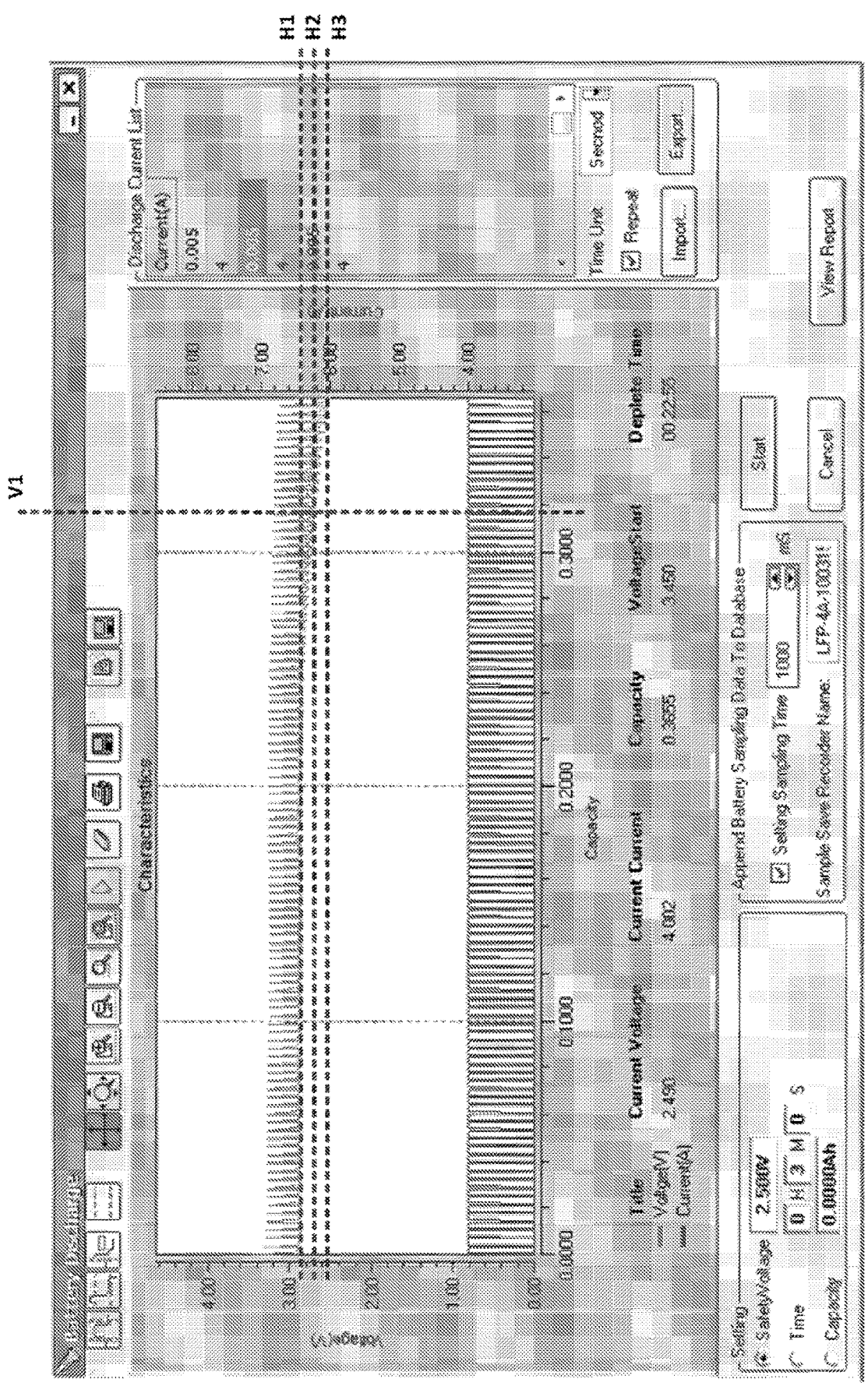
FIGS. 7, 8 and 9 are graphs of experimental data showing voltage (top line) and current (lower line) against used capacity during simulated use of an e-cigarette. For FIG. 7, the simulated use involves drawing repeated current pulses of 4 A from the battery, for FIGS. 8 and 9 the simulated use involves drawing repeated current pulses of 5 A from the battery. For FIGS. 7 and 8, the battery is a lithium iron phosphate (LFP) battery in accordance with some embodiments of the disclosure; for FIG. 9, the battery is a lithium manganese battery. In all cases, the battery has an AA form factor.

FIG. 7 is a graph showing experimental results from tests on an LFP battery to simulate behavior in an e-cigarette. The LFP battery under test had dimensions (form factor) corresponding to a standard AA battery. A succession of current pulses was drawn from the battery, each pulse having a current of approximately 4 A and a duration of 3 seconds to simulate an inhalation and the power supplied to operate the heater 365. This represents a total of approximately 3.3 mA hours for each inhalation. The interval between the inhalations was 10 seconds (shorter than in real usage, but allowing the experiment to be completed more quickly—and still allowing time for the heater to cool between inhalations). The current taken during these intervals was 0.005 A, for example to power controller 555. The total number of 4A current pulses until the battery fully discharged was 106, for a total operating time (including both pulses and pulse intervals) of approximately 1378 seconds (just under 23 minutes). The overall measured capacity of the battery was 0.365 A hours.

The graph of FIG. 7 plots the output voltage and output current from the LFP battery as measured against total capacity (energy, in Amp-hours) drawn so far from the battery. The x-axis (capacity) therefore also provides an indication of time, except that the intervals between pulses are heavily compressed along the x-axis (compared with their actual duration) because very little energy (capacity) was drawn during these intervals. The top plotted line in the graph of FIG. 7 represents output voltage (as per the scale to the left of the graph in volts), while the lower plotted line in FIG. 7 represents output current (as per the scale to the right of the graph in amps). The lower line clearly shows the individual current pulses, each of 4 amps. The top line clearly shows the drop in voltage which results from putting a load across the battery. In particular, for each current pulse, the battery voltage drops from the open circuit value (or very near open circuit value, given the 0.005 A current during the intervals between pulses) down by approximately 0.3-0.5 volts to the loaded value, when the 4 A current is being drawn.

Three horizontal lines, denoted H1, H2 and H3, have been superimposed on the plot of FIG. 7. The line H1 indicates the initial level of the minimum battery voltage under load; in fact, this minimum battery voltage remains approximately constant for the first half of the battery discharge lifetime (at least). The lines H2 and H3 are 0.16V and 0.32V respectively below line H1—representing a decrease compared with line H1 of approximately 5.6% and 11.2% respectively (or slightly under 5% and 10% respectively of the open circuit voltage). In addition, the vertical line $V^1$ indicates where the minimum voltage output from the battery (under load) is found to fall below the line H2. This only occurs once an energy of about 0.317 A hours has already been drawn from the battery, which represents about 87% of the overall capacity. In other words, FIG. 7 shows that the battery voltage under load for the LFP battery is constant within a range of ±3% for 85% of the discharge lifetime.

Table 1, shown in FIG. 10, is derived from the same underlying data set as FIG. 7, but is represented in tabular form. In particular, the main portion of Table 1 (i.e. all but the two columns to the far right, enclosed in the high-lighted box), represent the average voltage measurement under load for each successive current pulse. Thus the first row of FIG. 7 represents the voltage output under load for current pulses 1-10, the second row of FIG. 7 represents the voltage output under load for current pulses 11-20, and so on. The voltage was sampled at a rate of 1 Hz, so three voltage measurements were obtained for each current pulse (of 3 seconds), and then averaged together to provide the figures in Table 1. (Note also that a couple of boxes in Table 1 are left blank where the data did not record properly.) It will be appreciated that the voltage under load figures of Table 1 provide a good representation of the user experience of an e-cigarette incorporating such an LFP battery, in that the voltage under load figures reflect actual operation (inhalation) by the user (whereas the open circuit voltage figures represent intervals between user operation).

For the first half of the data (samples 1-53), the voltage output remains in the range 2.90-2.87V. This is a range of only just over 1%, and hence provides in effect a very constant output level. (The variations with this first half of the data may just reflect noise in the system, minor measurement variations, etc.) After 85% of the charge lifetime (samples 1-90), the average voltage under load has decreased by 0.15V from 2.90V to 2.75V. It will be appreciated that this is again a much smaller decline than would generally be seen for a more commonly used lithium battery.

Table 1 also shows that there is a further voltage drop of 0.13V as the remaining capacity is taken from the battery. Again, this is a much smaller decline than would generally be seen for a more commonly used lithium battery. In addition, a user is typically less likely to experience this voltage drop after 85% of the battery capacity has been used, because in many cases the e-cigarette will already provide some indication (e.g. a warning light) that the battery charge is at a relatively low level (15% or less), and therefore the user will re-charge the e-cigarette at this point (if not before). Moreover, a user is likely to accept that the low remaining battery charge may result in a slight decrease in performance, and indeed may take this as confirmation that the battery should now be re-charged.

In some cases, the battery voltage may be a little higher just at the start of operation, for the first couple of current pulses (inhalations) or so after the start of discharging from a fully charged state. There is a hint of this in FIG. 7, i.e. a very slight upturn at zero used capacity at the far left of the plot. Accordingly, it may be appropriate in some circumstances to discard the first one or two inhalations when assessing the initial voltage level. On the other hand, for the LFP battery that was tested, Table 1 shows that this effect is not really evident, or only marginally so, for the measured voltage under load of even the first current pulse.

The right-hand portion of Table 1 (shown in the highlighted outline) contains two columns. The first (left) one of these columns just provides the average voltage measurement for that row of the Table. This column gives a clear indication of the output voltage being approximately constant for the first half of the charge lifetime, and then a decrease setting in over the second half of the charge lifetime.

The second (right) one of the columns in Table 1 (the rightmost column in the overall table) represents the average decline in voltage within each pulse for the pulse samples in that row. Thus as mentioned above, three voltage measurements were obtained for each pulse, and in all cases there is a (small) decline in voltage output from the first measurement through to the third measurement. This decline was calculated for each pulse on an individual basis, and then averaged across the pulse samples for each row. This rightmost column shows that towards the end of the charge lifetime, not only does the average battery output fall, but also the rate of decline within an individual pulse also increases. However, this additional decline is of relatively lesser importance if the desired power profile over an individual inhalation broadly follows the shape shown in FIG. 6—i.e. a higher initial power output is important to first heat the heater, after which a reduced power output is generally acceptable.

Figure 8:
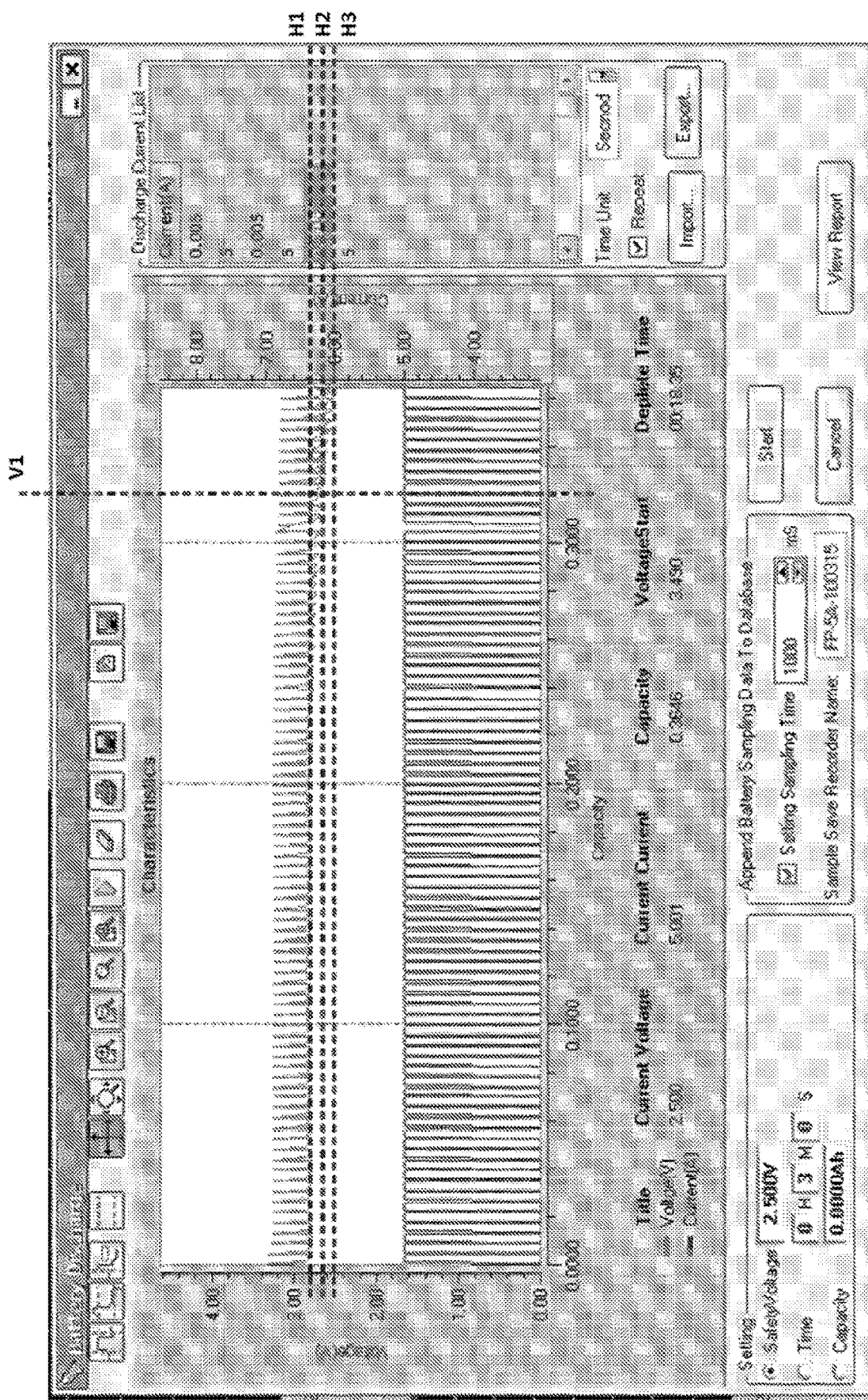

FIG. 8 is a plot generally similar to that of FIG. 7, and using the same battery, however, this time the current pulses are at 5A rather than 4 A. This is a relatively high level of current output, such as might be desired for the initial heating phase shown in FIG. 6 (and also helps to compensate for the lower voltage of an LFP battery compared to more commonly used batteries). As would be expected, the higher current level reduces the overall number of pulses that can be achieved over the charge lifetime (i.e. until the battery has been discharged), from 106 in FIG. 7, down to 86 for FIG. 8. Apart from this however, it can be seen that the LFP battery again produces a consistent and predictable voltage output which is effectively constant for a first half of the discharge cycle, and even then only undergoes a relatively mild decline in voltage during the second half of the discharge cycle. This is confirmed by a review of lines V1, H1, H2 and H3, which are provided on the same basis as for FIG. 7. Note that line V1, indicating a drop in voltage output under load of 0.16V, occurs once 0.321 A hours of capacity have been consumed from the battery, similar to the situation in FIG. 7 (where line V1 was positioned at a capacity of 0.317 A hours).

Figure 9:
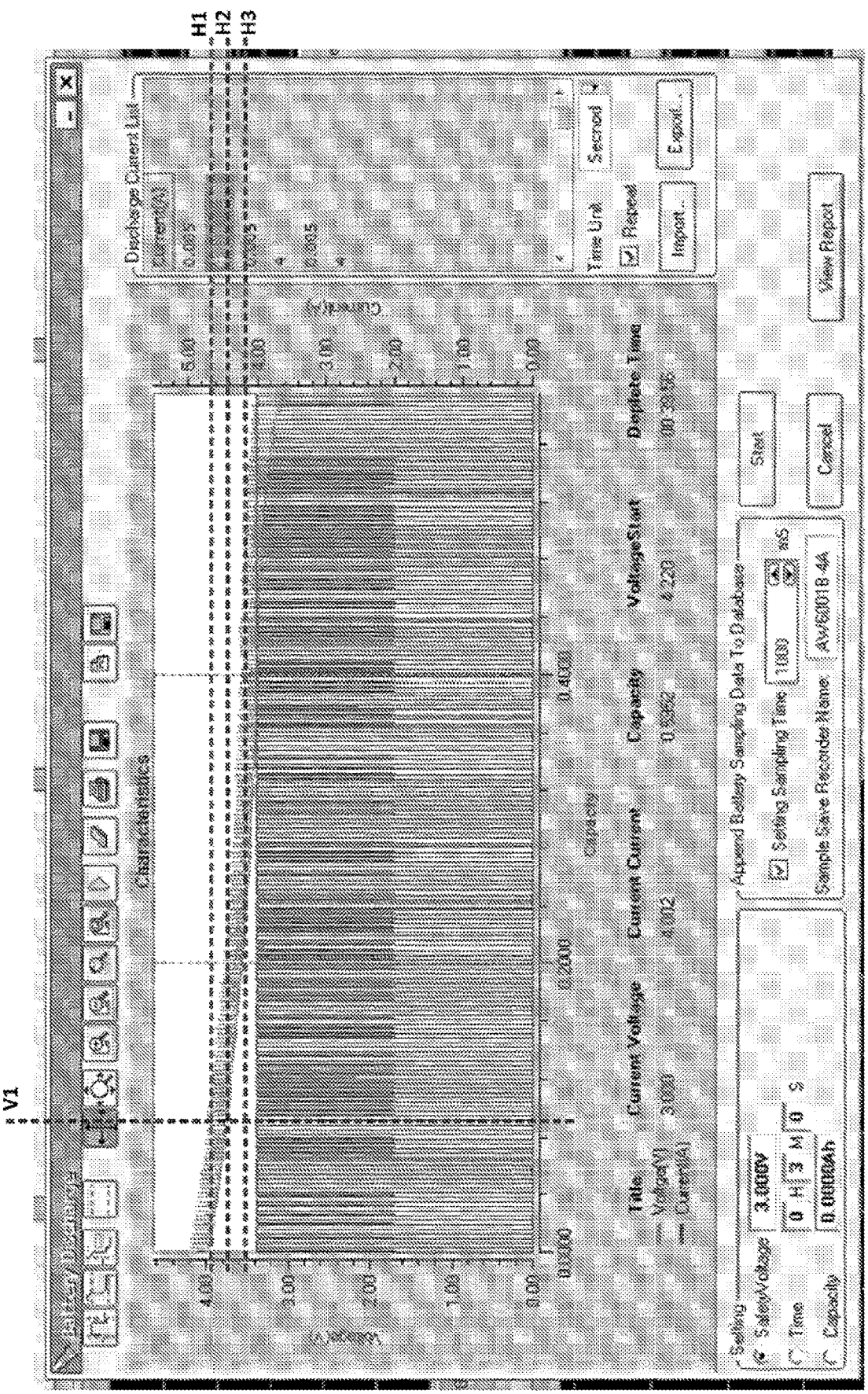

FIG. 9 is a plot generally similar to that of FIG. 8, again using 5 A current pulses and showing a plot of voltage (top line) and current (lower line) against used capacity (in A hours). The battery tested in FIG. 9 is a lithium manganese cathode cell, rather than an LFP cell. The form factor of the lithium manganese battery is AA (the same as that of the LFP battery for FIGS. 7 and 8).

As shown in FIG. 9, the lithium manganese battery does have an advantage of higher capacity than the LFP cell of FIGS. 7 and 8. In particular, the lithium manganese battery is found to have a capacity of 0.595 A hours, which supported 184 current pulses at 5A. However, the profile of voltage variation with capacity for the lithium manganese battery is significantly poorer than the corresponding profile for an LFP battery as shown in FIGS. 7 and 8. This can be seen by looking at lines V1, H1, H2 and H3 which have again been superimposed on the plot, with H1 representing the voltage level under load at zero used capacity.

The spacing of lines H1, H2 and H3 has been increased to 0.21V (compared with 0.16V in FIGS. 7 and 8—to reflect the greater initial voltage for the lithium manganese battery compared with the LFP battery, e.g. about 4.2V open circuit compared with 3.4V open circuit). However, even with this greater spacing, we see from the positioning of line V1 that the voltage under load crosses line H2 (hence a 0.21V drop from zero used capacity) at a used capacity of just 0.085 A hours. This represents just 14% of the overall capacity of the lithium manganese battery. Indeed, in FIG. 8 the LFP battery crossed the line H2 at a capacity of 0.32 A hours, so even though the LFP battery has a lower total capacity than the lithium manganese battery, it can supply a much greater capacity (both in relative and also absolute terms) at an approximately constant voltage. Furthermore, the LFP battery exhibits a very consistent voltage output level until a capacity of about 0.2 A hours has been used, and only then starts to decline towards line H2. In contrast, in FIG. 9, it is clear that the output voltage under load of the lithium manganese battery starts to drop even after the very first few current pulses.

In addition, not only does the output voltage of the lithium manganese battery start to decline at a very low used capacity, but this decline continues through the lifetime of the battery charge, so that the overall voltage drop of the lithium manganese battery during a discharge cycle is much greater than for an LFP battery. For example, in FIG. 8, the voltage output under load only reaches line H3 (0.32V below the initial voltage level) once the battery is fully discharged (used capacity about 0.36 A hours). In contrast, for FIG. 9, the voltage output under load reaches line H3 (0.42 V below initial voltage level) at a lower used capacity of about 0.24 A hours, and continues to drop by at least the same amount again before the lithium manganese battery is fully discharged.

The plots of FIGS. 7, 8 and 9 confirm that an e-cigarette having an LFP battery as disclosed herein is able to provide more consistent and predictable performance, especially in terms of the voltage supply for heater operation at each inhalation, but without involving more costly or complex electronics. Such a battery may be utilized in a wide range of electronic vapor provision systems, for example, for vaporizing nicotine-containing liquids or for producing volatiles from tobacco-derived plant material (or derivatives thereof).

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc., other than those specifically described herein. The disclosure may include other inventions not presently claimed, but which may be claimed in future.

The invention claimed is:

1. A control unit for an electronic vapor provision system, the control unit comprising:
a battery for providing electrical power to a heater and wherein an output voltage of the battery when 80% discharged by successive puffs of the electronic vapor provision system is no more than 0.25V below the output voltage of the battery when fully charged.

2. The control unit of claim 1, wherein the battery is a lithium iron phosphate battery having a lithium ferrophosphate cathode.

3. The control unit of claim 1, wherein the battery has a rated capacity in a range of 250-600 mA hours to support at least 100 puffs of the electronic vapor provision system, each puff drawing a current of at least 2.5 A from the battery.

4. The control unit of claim 1, wherein the control unit further includes a sensor to detect a user inhalation, and a controller configured to initiate provision of electrical power from the battery to the heater in response to the sensor detecting the user inhalation.

5. The control unit of claim 4, wherein in response to the sensor detecting the user inhalation, the controller is configured to provide a first phase of electrical power and then a second phase of electrical power from the battery to the heater, wherein the first phase of electrical power has a higher level of electrical current than the second phase of electrical power.

6. The control unit of claim 5, wherein the first phase of electrical power has a current level of equal to or greater than 3 amps.

7. The control unit of claim 6, wherein the first phase of electrical power has a current level of equal to or greater than 5 amps.

8. The control unit of claim 1, wherein the output voltage of the battery when half discharged is no more than 0.1V below the output voltage of the battery when fully charged.

9. The control unit of claim 8, wherein the output voltage of the battery when half discharged is no more than 0.05V below the output voltage of the battery when fully charged.

10. The control unit of claim 1, wherein the output voltage of the battery when half discharged is no more than 3% below the output voltage of the battery when fully charged.

11. The control unit of claim 8, wherein the output voltage of the battery when half discharged is no more than 1.5% below the output voltage of the battery when fully charged.

12. The control unit of claim 1, wherein the output voltage of the battery when 80% discharged is no more than 0.16V below the output voltage of the battery when fully charged.

13. The control unit of claim 1, wherein the output voltage of the battery when 80% discharged is no more than 6% below the output voltage of the battery when fully charged.

14. The control unit of claim 1, wherein the output voltage of the battery is measured under load when providing electrical power to the heater to produce vapor.

15. The control unit of claim 14, wherein the output voltage of the battery is in a range of 2.6V-3V measured under load.

16. The control unit of claim 15, wherein the output voltage of the battery is approximately 2.8V measured under load.

17. The control unit of claim 1, wherein the output voltage of the battery is in a range of 3V-3.4V for an open circuit.

18. The control unit of claim 17, wherein the output voltage is approximately 3.2V for an open circuit.

19. The control unit of claim 1, wherein electrical power is supplied from the battery to the heater without compensation for variation in output voltage of the battery over a discharge cycle.

20. An electronic vapor provision system comprising the control unit of claim 1 and the heater.

21. The electronic vapor provision system of claim 20, wherein the heater is located in a cartomizer that is connected to the control unit.

22. The electronic vapor provision system of claim 20, wherein the heater and the control unit are integrated into a single device.

* * * * *